United States Patent [19]

Palefsky et al.

[11] Patent Number: 5,428,022
[45] Date of Patent: Jun. 27, 1995

[54] COMPOSITION OF LOW TYPE III CONTENT HUMAN PLACENTAL COLLAGEN

[75] Inventors: Howard Palefsky, Atherton; Bruce B. Pharriss, Palo Alto; George Chu, Cupertino, all of Calif.

[73] Assignee: Collagen Corporation, Palo Alto, Calif.

[21] Appl. No.: 921,810

[22] Filed: Jul. 29, 1992

[51] Int. Cl.⁶ .................. C07K 14/00; C07K 5/08; A61F 2/14; A61B 19/00
[52] U.S. Cl. .................... 514/21; 530/356; 106/124
[58] Field of Search .............. 530/356; 514/21; 106/124

[56] References Cited

U.S. PATENT DOCUMENTS

| | | | |
|---|---|---|---|
| 4,226,858 | 10/1980 | Pfirrmann | 424/195 |
| 4,957,902 | 9/1990 | Grinnell | 514/17 |
| 5,043,426 | 8/1991 | Goldstein | 530/356 |

*Primary Examiner*—Howard E. Schain
*Assistant Examiner*—Lynn P. Touzeau
*Attorney, Agent, or Firm*—Morrison & Foerster

[57] ABSTRACT

A human placental collagen composition for use in soft tissue augmentation comprising an aqueous suspension of a homogenized nonirradiation-sterilized mixture of type I and type III human placental collagen, wherein the type III collagen constitutes less than about 10% by weight of the mixture.

17 Claims, No Drawings

COMPOSITION OF LOW TYPE III CONTENT HUMAN PLACENTAL COLLAGEN

TECHNICAL FIELD

The present invention is in the field of collagen compositions for medical use and relates specifically to placenta-derived human collagen having a low type III content.

BACKGROUND

Collagen is the major fibrous protein of many animals. It accounts for about 30% of the total human body protein. Collagen constitutes the fibrillar component of the soft connective tissues (e.g., skin, ligament and tendon) and is the major component of the calcified tissues such as bone and dentin.

Collagen is composed of three proline/ hydroxyproline-rich polypeptide chains. There are known to be at least 12 genetically distinct forms of collagen. Four main types (I, II, III, and IV) have been characterized. Type I is the major portion of both soft and hard connective tissue. Type II collagen is the major collagen of cartilage. Type III is found in blood vessels, fetal membranes, and wounds. Basement membrane collagens are classified as type IV.

Injectable bovine collagen has been marketed for soft tissue augmentation since the early 1980s. This collagen is derived from bovine hide and is prepared by solubilizing the hide in acid, proteolytically digesting the soluble collagen to remove telopeptides, and purifying the atelopeptide collagen. The collagen is subsequently sterilized by submicron filtration and then reconstituted. Two forms of this collagen—one uncrosslinked and the other lightly crosslinked—are currently marketed under the trademarks ZYDERM® and ZYPLAST®, respectively. Both forms comprise about 95% type I collagen and 5% type III collagen.

Human collagen has been proposed as a biomaterial for numerous indications, including soft tissue augmentation. Human collagen has the advantage of being less immunogenic than bovine-derived collagen. It has the disadvantage of requiring additional processing steps to ensure the elimination of human pathogens such as viruses.

U.S. 5,002,071 describes an injectable human collagen formulation for soft tissue augmentation in which the collagen is chorion and/or amnion collagen. The amnion/chorion is isolated from other placental tissues, homogenized, digested with proteases, reconstituted, and sterilized and crosslinked by gamma irradiation. The patent (col. 10, line 37 et seq.) indicates that the injectable human amnion collagen has a much larger proportion of type III collagen to type I collagen (43:57) than the bovine ZYDERM® and ZYPLAST® products. The patent and its prosecution history indicate that type III collagen has greater crosslinking than type I and is thus more persistent than type I.

The present invention relates to a collagen material that is derived from total placental tissue rather than just amnion/chorion tissue, is depleted of type III collagen to 10% by weight or below, and is sterilized by means other than irradiation. Contrary to the statements in U.S. 5,002,071, this type III depleted human collagen is more persistent than human collagen containing relatively large amounts of type III collagen.

DISCLOSURE OF THE INVENTION

The present invention is a composition for medical use comprising a homogenized nonirradiation-sterilized mixture of type I and type III human placental collagen wherein the type III collagen constitutes less than about 10% by weight of the mixture.

MODES FOR CARRYING OUT THE INVENTION

Characterization of Human Collagen

The human collagen of the present invention is distinct from the human collagen composition described in U.S. 5,002,071 in three major respects: (1) it is derived from total placental tissue (the entire placenta, including the amnion, chorion, and other placental tissue), rather than from only the amnion and/or chorion; (2) it is depleted of type III collagen and contains much less type III collagen than the patented composition; and (3) it is not sterilized by irradiation. The first distinction is important from the standpoint of manufacturing and yield of product per placenta processed. As total placental tissue is used, there is no need to manually separate the amnion/chorion. The collagen component in the entire placental tissue, rather than just the amnion/chorion, is recovered. The second distinction is believed to provide the invention implant with improved persistence (longevity), as it is known that type III collagen is resorbed more rapidly than type I collagen. Furthermore, applicants evaluated a purified formulation of human placental collagen of 40% type I and 60% type III and found it to be only partially soluble in acid and deficient in its ability to be reconstituted into fibers. Finally, the third difference avoids employing a sterilization technique (irradiation) that may alter the composition (i.e., by crosslinking) of the collagen in an undesirable and/or unreproducible manner.

The injectable compositions of this invention comprise about 20 to about 120 mg/ml, preferably about 30 to 100 mg/ml, of human reconstituted (i.e., fibrillar) placental collagen suspended in a physiologically acceptable injectable carrier. The collagen itself is obtained from total placental tissue, is at least about 95% soluble in pH 2 HCl at 20° C., is composed of type I and type III collagen in a weight ratio of at least about 9:1, and contains less than about 10 μg carbohydrate/mg collagen. The carrier is preferably saline containing $Na_2HPO_4$, with or without lidocaine. Alternatively, the collagen may be formulated with a pharmaceutically acceptable nonaqueous carrier.

Preparation of Human Collagen

Human placentas are preferably obtained from known donors who have tested negative for hepatitis viruses and HIV. The placentas are first acid and ethanol washed to remove blood and extraneous debris. The washed placental tissue is then treated with protease (e.g., pepsin) at low pH (2-3) to solubilize the collagen. The solubilized collagen is treated via a series of salt fractionations at acid and neutral pHs to reduce the type III content of the collagen to below about 10% by weight. The type I-enriched collagen is solubilized in acid, filtered, reconstituted from solution and washed with acetone. The resulting collagen powder is again solubilized in acid and sterile-filtered. For use as an injectable material for soft tissue augmentation, the collagen is precipitated from the sterile filtered solution (with or without crosslinking via addition of a bifunctional chemical crosslinking agent such as glutaraldehyde or polyethylene glycol), homogenized, and resuspended in the physiologically acceptable vehicle. The suspension is loaded into syringes for injection. The suspension should be injectable through a 32-gauge or larger diameter needle.

Uses of Human Collagen

The human collagen of this invention may be used in any one of the many uses for which purified bovine collagen has been employed. It may be used to augment soft tissue to treat a large number of congenital anomalies, acquired defects or cosmetic defects. Examples are congenital anomalies such as hemifacial microsomia, malar and zygomatic hypoplasia, unilateral mammary hypoplasia, pectus excavatum, pectoralis agenesis (Poland's anomaly), and velopharyngeal incompetence secondary to cleft palate repair or submucous cleft palate (as a retropharyngeal implant); acquired defects (post-traumatic, post-surgical, post-infectious) such as depressed scars, subcutaneous atrophy (e.g., secondary to discoid lupis erythematosus), enophthalmos in the enucleated eye (also superior sulcus syndrome), acne pitting of the face, linear scleroderma with subcutaneous atrophy, saddle-nose deformity, Romberg's disease, and cosmetic defects such as glabellar frown lines, deep nasolabial creases, circumoral geographical wrinkles, sunken cheeks and mammary hypoplasia.

Other soft tissue augmentation uses are to repair or augment sphincters such as the urinary or anal sphincter for treating incontinence.

It may be formed into membranes, sheets, tubes, or other shaped articles such as lenticules, as described in U.S. Pat. Nos. 4,600,533; 4,655,980; and 4,725,671 and used in the medical applications that employ biocompatible shaped articles such as burn treatment, tendon repair, or wound repair. Cross-linked compositions of the invention may be used in the form of a dehydrated particulate material.

It may be mixed with minerals, bone marrow or other particulate materials for use in hard tissue augmentation repair (e.g., bone, cartilage, or dental repair) as described in U.S. Pat. Nos. 4,743,229; 4,776,890; 4,775,467; 4,774,227; 4,789,663.

It may be formed into a matrix such as the sponge described in U.S. Pat. No. 5,024,841 which may serve as a carrier for growth factors or drugs.

It may be coated onto prostheses as described in U.S. Pat. No. 4,772,285.

The disclosures of the above-mentioned patents relating to such uses are herein incorporated by reference.

The following examples further illustrate the preparation of the human collagen of the invention and its properties. These examples are not intended to limit the invention in any manner.

Production of Human Collagen

Human placenta was cut into small pieces and mixed with citric acid. The mixture was passed through a press filter and the filtrate discarded. The acid-washed tissue was washed several times with ethanol and press-filtered to remove placental blood from the tissue. The tissue was then mixed with NaCl and again press-filtered.

The washed tissue was digested in citric acid buffer to pH 2.4 containing pepsin T1000 (155g/100kg) for 15 hr. The digest was diluted with citric acid and NaCl and centrifuged. The residual tissue was redigested in citric acid buffer to pH 2.4 containing pepsin T1000 (455 g/L) for 90 hr. The digest was diluted with citric acid as above and centrifuged.

The supernatant was purified by NaCl fractionation. The precipitate from the NaCl fractionation was digested in citric acid to pH 2.4, NaCl, and pepsin T1000 for 60 hr. The digest was centrifuged and the supernatant purified by NaCl fractionation at neutral pH.

The precipitate was dissolved in HCl and NaCl and the solution filtered. Collagen was precipitated from the filtrate by addition of NaCl; the mixture was allowed to stand for 15 hr, then centrifuged. The resulting solids were washed several times with acetone and dried with sterile air.

The resulting collagen powder comprised less than 10% type III (as determined by SDS-PAGE) with the remainder type I. Salt content was less than 10%, heavy metals $\leq 20$ ppm, carbohydrates $<10$ µg/mg collagen, and endotoxin concentration $<0.3$ endotoxin units/mi. This powder was dissolved in HCl, pH2, and desalted by ultrafiltration. The desalted collagen solution was prefiltered and sterile-filtered into autoclaved storage containers. Collagen was precipitated from the solution by addition of $Na_2HPO_4$ and increasing the pH to about 7.2. The precipitated collagen was homogenized by recirculation through a peristaltic pump with 0.02M $Na_2HPO_4$, 0.13M NaCl, containing 0.3% lidocaine and aseptically loaded into sterile syringes. The syringes are stored at 10° C. pending use.

In Vitro Immunological Testing

This testing was carried out to determine whether the human collagen prepared as above would react with sera from patients with known hypersensitivity to bovine collagen (ZYDERM ® collagen implant, ZCI).

Procedure

Acid solubilized fibrillar human placental collagen (HCI) suspensions prepared as above at an initial concentration of 1 mg/ml were used to coat multiwell plates for ELISA testing. Production grade ZCI was used for comparison.

Thirty-two sera from patients with known hypersensitivity reactions to ZCI (antibody titers $\geq 160$) were stored at $-80°$ C. and used within one year. Peroxidase-labeled detecting antibody (goat anti-human immunoglobulin) was obtained from a commercial source. Rabbit anti-bovine dermal collagen and normal human serum were used as positive and negative controls respectively.

Sera were tested using an enzyme-linked immunoadsorption assay (ELISA). Briefly, sera from patients with hypersensitivity to bovine collagen were diluted and added to antigen-coated wells at room temperature for 45 min. After incubation, plates were washed and enzyme-labeled anti-immunoglobulin added for an additional 45 min. After incubation plates were again washed, developed with ABTS (a peroxidase substrate) and the color read at an absorbance of 414 nm. The cross-reactivity of human antibodies to bovine collagen with human placental collagen was additionally tested in a competitive inhibition ELISA. The initial absorption with optimally diluted antigens was carried out in glass test tubes overnight at 4° C. with shaking. Aliquots of preabsorbed antisera were then tested against competing antigens in an identical indirect ELISA system.

Results

Sera from patients with demonstrated antibodies to ZCI showed no measurable binding to HCI while retaining their ability to react with ZCI. Rabbit anti-bovine dermal collagen antisera served as a positive control. Normal human sera were negative for antibodies to both human and bovine collagen.

In a competitive inhibition ELISA, only bovine collagen preabsorption reduced the attachment to ZCI coated plates of antibodies from patients with hypersensitivity to ZCI. HCI preabsorption was ineffective, confirming the results seen in the direct immunoassay.

In Vivo Testing

Animal Models: HCI (35 mg/ml) was injected into the right and left suprascapular subcutaneous space (0.5 cc each) of 12 adult male Sprague-Dawley rats. An equal number of rats received ZCI. Four animals for each material were sacrificed at days 7, 30 and 90 days post-injection. Explants were wet weighed, then fixed in neutral buffered formalin and processed for histologic examination.

Human collagen (0.1 cc each) was also injected as a focal bolus into the dorsolateral dermis of an anesthetized domestic pig on 4 separate occasions—days 30, 14, 7 and 0 prior to sacrifice. The opposite flank of the pig was treated with ZCI. Thirty-two explants (2 materials×4 time points×4 samples) were fixed and processed as mentioned above. Paraffin-embedded specimens from both experiments were sectioned; stained with hematoxylin and eosin, and Trichrome stain; and evaluated microscopically. The lateral extent and horizontal distribution of porcine dermal injection sites were evaluated semiquantitatively and with an ocular micrometer.

Results in Animal Studies

Rat: After 7 days in vivo in the rat subcutis, both human and bovine collagen implants were largely cohesive and demonstrated minimal host fibroblast colonization and peripheral fibrosis. A mild inflammatory response was evident in the connective tissue adjoining the human collagen implants that was somewhat more extensive than seen in the ZCI counterparts. The inflammatory cell populations in response to both materials (both of which are xenogeneic in the rat) consisted of granulocytes as well as some small lymphocytes and macrophages. Wet weights for all explants were comparable at this time point.

At 30 days, human collagen implants had a fibrillar character that was highly similar to ZCI, but with a slightly more finely divided structure than ZCI. The host connective tissue infiltrate indicated a high degree of biocompatibility, including some adipose colonization as well as a thickened fibrous condensation in the surrounding tissues. A benign lymphohistocytic infiltrate was still evident at this time. Bovine collagen implants were generally quite similar in appearance. Although some calcification was detected with bovine collagen, this reaction has been observed with collagen implants in the rat subcutis and is unique to rodent species. This mineral accumulation may have contributed to the weight increase for ZCI over HCI seen at this intermediate time point. Calcification was not observed in human placental collagen implants.

At 90 days HCI implants were still detectable in the rat subcutis, and the collagen fibers were even more finely divided and often extensively colonized by host adipocytes. The inflammatory response had completely resolved by this time. Bovine collagen implants continued to calcify, a characteristic that ZYDERM ® collagen does not exhibit when placed in the human dermis.

Pig: No host connective tissue implant colonization or inflammatory response was evident in any onset samples taken from porcine dermal injection sites. Both HCI and ZCI implants occupied superficial, mild and deep dermal planes as well as subcutaneous positions. There were some differences between materials in the extent of lateral intrusion; with HCI spreading marginally farther on injection, probably due to its less robust or finer fibrillar characteristics.

At day 7, both materials were only slightly colonized, with fibroblasts found only at the periphery of implants that were distributed predominantly in the mid-deep dermis and subcutaneum. Neither material showed any significant increase in lateral spread, indicating little displacement from the original injection site. Human collagen produced a moderate lymphohistocytic perivascular inflammatory response with an eosinophilic component at this time point. Infiltration of eosinophilic cells into collagen implants is a common and biocompatible occurrence in rodent and porcine models. The cellular immune response to ZCI was similar but somewhat milder.

By two weeks, implant colonization was still minimal for both materials. Loss of HCI deep in the subcutis was somewhat more advanced than for ZCI. The inflammatory response to HCI continued although generally reduced in extent and intensity, while the inflammatory response to ZCI was completely resolved.

By 30 days, ZCI implants were moderately colonized by fibroblasts with an occasional giant cell and no small cell response remaining. These implants were frequently located in the subcutaneum. Human collagen colonization lagged behind that seen in ZCI and the implants were located exclusively in the subcutaneum, often reduced in lateral extent, and occupied less volume. The inflammatory response to HCI was now only a very mild lymphoid infiltrate seen associated with some implants.

In summary, HCI was eminently biocompatible in the rat subcutaneum and the porcine dermis. It must be remembered that human collagen is xenogeneic in these recipients as bovine collagen (ZCI) is also. HCI exhibited only a mild transient inflammatory response, similar to ZCI.

In Vivo Human Studies

Clinical Protocol

A double-blind study was conducted at 2 centers. Patients received intradermal injections of 0.1 cc each of HCI and ZCI into the volar surface of opposite forearms or the skin behind opposite ears. Follow-up visits were scheduled for 7, 21, and 30 days following the injections. At each follow-up visit, photographs were taken and clinical observations made to document the presence of clinical hypersensitivity symptoms including erythema, swelling, induration, pruritus and tenderness. Physicians were asked to describe each site as a positive or negative test. For purposes of this study, a positive test was defined as erythema or induration present for greater than forty-eight hours, whether or not it was accompanied by either swelling or pruritus. Biopsies were performed on both implant sites. Biopsies were scheduled at either day 7 or day 30. Phlebotomy was performed at the following intervals: pre-test implantation, at the time of biopsy, and at day 30. Specimens were evaluated by ELISA for the presence of anti-collagen antibodies.

Patient inclusion criteria called for healthy patients with a documented history of a hypersensitivity response to a bovine collagen test or treatment. Subjects were excluded if their treatment reaction had been within the past two years or if they had experienced systemic symptoms following prior bovine collagen exposure. Other evaluation criteria included a history of anaphylactoid or anaphylactic reactions, patients on immunosuppressant therapy, and pregnant or nursing women.

Results

Six caucasian females with a mean age of 45 were selected for enrollment in the study. The age range was from 29 to 61. All six patients (designated 101, 102, 103, 104, 201, 202) had a history of a positive skin test; none had continued ZCI treatments.

Patient 101 had erythema, swelling, and induration (14 mm) accompanied by pruritus and pain in the right forearm (ZCI). The left arm (HCI) demonstrated 4 mm of erythema with no other signs or symptoms. These sites were biopsied at day 7. The preliminary histological results on subject 101 indicate a moderate lymphocytic infiltrate in the site from the right arm which is consistent with a hypersensitivity reaction to the collagen implant. The results from the biopsy of the left arm do not indicate any unusual inflammation and do not suggest any evidence of hypersensitivity.

At days 7 and 21 of follow-up, patient 102 had no clinical signs or symptoms at the skin test site in the right arm (HCI), but displayed 18 mm of erythema at the skin test site in the left arm (ZCI).

After 7 days post-injection, patient 103 demonstrated 18 mm of erythema, 12 mm of induration, and swelling with pruritus and pain at the test implant site in the right arm (ZCI), while the left arm (HCI) had 4 mm of erythema only. At day 21 of follow-up, the right arm (ZCI) of this subject was still reacting as a positive skin test, but there were no clinical signs or symptoms at the skin test site in the left forearm.

Patient 104 reported a history of erythema, swelling and induration on both right (HCI) and left (ZCI) forearms which lasted for 36 hours after the injections. She described the right side (HCI) as being a slightly more prominent reaction than the left side (ZCI). Patient 104 had no clinical symptoms meeting the criteria for a positive test at either implant site. No inflammatory response was seen histologically and no anti-bovine collagen antibody titers were measurable.

Patient 201 received the injections behind the ears. At day 7 she displayed 4 mm of erythema and induration on the right side (ZCI) accompanied by itching during the first 2 days. There were no signs or symptoms at the skin test site behind the left ear (HCI).

Patient 202 experienced erythema, swelling and induration on the left forearm (ZCI) which were still visible at day 7. There were no symptoms present on the right forearm (HCI).

Modifications of the above-described modes for carrying out the invention that are obvious to those of skill in the fields of biochemistry, medicine, and related fields are intended to be within the scope of the following claims.

We claim:

1. A composition for medical use comprising a homogenized, nonirradiation-sterilized mixture of fibrillar type I and type III human placental collagen wherein the type III collagen constitutes less than about 10% by weight of the mixture.

2. The composition of claim 1 wherein the collagen is obtained from total placental tissue.

3. The composition of claim 1 wherein the collagen is at least 95% soluble in pH 2 HCl at 20° C., and contains less than 10 μg carbohydrate per mg collagen.

4. The composition of claim 1 wherein the mixture is an aqueous suspension and the collagen in the suspension has a concentration in the range of about 20 to about 120 mg/ml.

5. The composition of claim 1 wherein the collagen is not crosslinked.

6. The composition of claim 1 wherein the collagen is crosslinked with a chemical crosslinking agent.

7. The composition of claim 6 wherein the crosslinking agent is glutaraldehyde or polyethylene glycol.

8. An injectable formulation of the composition of claim 1.

9. A mixture of the composition of claim 1 and a mineral, which mixture is suitable for hard tissue repair.

10. A membrane of the composition of claim 1.

11. A prosthesis coated with the composition of claim 1.

12. The composition of claim 1 in combination with a pharmaceutical.

13. The composition of claim 1 in the form of a sponge.

14. The composition of claim 6 in the form of a tube or sheet.

15. The composition of claim 6 in the form of a dehydrated particulate material.

16. The composition of claim 15 further comprising a pharmaceutically acceptable, nonaqueous carrier.

17. The composition of claim 1 in the form of a lenticule.

* * * * *